US010959826B2

(12) United States Patent
Skender et al.

(10) Patent No.: US 10,959,826 B2
(45) Date of Patent: Mar. 30, 2021

(54) SUPPORT STRUCTURE FOR SCALLOPED GRAFTS (71) Applicant: Cook Medical Technologies LLC, Bloomington, IN (US)

(72) Inventors: Davorin K. Skender, Bloomington, IN (US); Blayne A. Roeder, Bloomington, IN (US)

(73) Assignee: Cook Medical Technology LLC, Bloomington, IN (US)

( * ) Notice: Subject to any disclaimer, the term of this patent is extended or adjusted under 35 U.S.C. 154(b) by 281 days.

(21) Appl. No.: 15/956,034

(22) Filed: Apr. 18, 2018

(65) Prior Publication Data

US 2018/0228594 A1 Aug. 16, 2018

Related U.S. Application Data (63) Continuation-in-part of application No. 14/875,925, filed on Oct. 6, 2015, now Pat. No. 10,758,387.

(60) Provisional application No. 62/487,108, filed on Apr. 19, 2017, provisional application No. 62/064,595, filed on Oct. 16, 2014.

(51) Int. Cl.
A61F 2/07 (2013.01)
A61F 2/06 (2013.01)

(52) U.S. Cl.
CPC .......... A61F 2/07 (2013.01); A61F 2002/065 (2013.01); A61F 2210/0023 (2013.01); A61F 2230/0013 (2013.01); A61F 2230/0054 (2013.01); A61F 2230/0093 (2013.01)

(58) Field of Classification Search
CPC .................. A61F 2/07; A61F 2002/061; A61F 2002/065; A61F 2210/0023; A61F 2230/0013; A61F 2230/0054; A61F 2230/0093
See application file for complete search history.

(56) References Cited

U.S. PATENT DOCUMENTS

| 4,902,508 | A | 2/1990 | Badylak et al. |
| 4,907,336 | A | 3/1990 | Gianturco |
| 5,387,235 | A | 2/1995 | Chuter |
| 5,591,230 | A | 1/1997 | Horn et al. |
| 5,617,878 | A | 4/1997 | Taheri |

(Continued)

FOREIGN PATENT DOCUMENTS

| EP | 2 803 340 A1 | 11/2014 |
| EP | 2803340 A1 | 11/2014 |

(Continued)

OTHER PUBLICATIONS

European Search Report for corresponding EP Application No. 18275052, dated Jun. 25, 2018, 7 pages.

(Continued)

Primary Examiner — Kathleen S Holwerda
Assistant Examiner — Brooke Labranche
(74) Attorney, Agent, or Firm — Brinks Gilson & Lione (57) ABSTRACT A support structure for a three-sided scallop in the edge of a stent graft including two substantially longitudinal perimeter support sections and an undulating lateral side base extending between the two support sections. The undulations extend below the edge of the lateral side of the scallop and overlap the graft material away from the edge of the lateral side.

19 Claims, 5 Drawing Sheets

(56) References Cited

U.S. PATENT DOCUMENTS

| | | |
|---|---|---|
| 5,653,743 A | 8/1997 | Martin |
| 5,709,713 A | 1/1998 | Evans et al. |
| 5,711,969 A | 1/1998 | Patel et al. |
| 5,720,776 A | 1/1998 | Chuter et al. |
| 5,733,337 A | 3/1998 | Carr, Jr. et al. |
| 5,755,778 A | 5/1998 | Kleshinski |
| 5,769,882 A | 6/1998 | Fogarty et al. |
| 5,782,904 A | 7/1998 | White et al. |
| 5,885,619 A | 3/1999 | Patel et al. |
| 5,906,640 A | 5/1999 | Penn et al. |
| 5,921,995 A | 7/1999 | Kleshinski |
| 5,955,110 A | 9/1999 | Patel et al. |
| 5,961,548 A | 10/1999 | Shmulewitz |
| 5,968,096 A | 10/1999 | Whitson et al. |
| 5,984,955 A | 11/1999 | Wisselink |
| 6,042,605 A * | 3/2000 | Martin ............... A61F 2/07 623/1.13 |
| 6,056,775 A | 5/2000 | Borghi et al. |
| 6,077,296 A | 6/2000 | Shokoohi et al. |
| 6,099,558 A | 8/2000 | White et al. |
| 6,187,033 B1 | 2/2001 | Schmitt et al. |
| 6,203,568 B1 | 3/2001 | Lombardi et al. |
| 6,206,931 B1 | 3/2001 | Cook et al. |
| 6,210,429 B1 | 4/2001 | Vardi et al. |
| 6,221,102 B1 | 4/2001 | Baker et al. |
| 6,261,273 B1 | 7/2001 | Ruiz |
| 6,287,315 B1 | 9/2001 | Wijeratne et al. |
| 6,287,330 B1 | 9/2001 | Johansson et al. |
| 6,325,826 B1 | 12/2001 | Vardi et al. |
| 6,334,867 B1 | 1/2002 | Anson |
| 6,344,052 B1 | 2/2002 | Greenan et al. |
| 6,395,018 B1 | 5/2002 | Castaneda |
| 6,409,750 B1 | 6/2002 | Hyodoh et al. |
| 6,428,565 B1 | 8/2002 | Wisselink |
| 6,524,335 B1 | 2/2003 | Hartley et al. |
| 6,558,418 B2 | 5/2003 | Carpentier et al. |
| 6,648,722 B2 | 11/2003 | Lynders et al. |
| 6,890,340 B2 | 5/2005 | McGuckin, Jr. et al. |
| 6,939,370 B2 | 9/2005 | Hartley et al. |
| 6,974,471 B2 | 12/2005 | Van Schie et al. |
| 7,011,679 B2 | 3/2006 | Lauterjung |
| 7,105,020 B2 | 9/2006 | Greenberg et al. |
| 7,232,459 B2 | 6/2007 | Greenberg et al. |
| 7,238,198 B2 | 7/2007 | Hartley et al. |
| 7,273,459 B2 | 9/2007 | Desilets et al. |
| 7,294,147 B2 | 11/2007 | Hartley et al. |
| 7,413,573 B2 | 8/2008 | Hartley |
| 7,438,721 B2 | 10/2008 | Doig et al. |
| 7,537,606 B2 | 5/2009 | Hartley et al. |
| 7,708,771 B2 | 5/2010 | Chuter et al. |
| 7,722,657 B2 | 5/2010 | Hartley |
| 7,803,177 B2 | 9/2010 | Hartley et al. |
| 8,518,098 B2 | 8/2013 | Roeder et al. |
| 8,926,686 B2 | 1/2015 | King |
| 9,060,887 B2 | 6/2015 | Hartley et al. |
| 9,072,261 B2 | 7/2015 | Hartley et al. |
| 9,095,458 B2 | 8/2015 | Hartley et al. |
| 9,539,123 B2 | 1/2017 | Hartley et al. |
| 2002/0052648 A1 | 5/2002 | McGuckin, Jr. et al. |
| 2003/0088305 A1 | 5/2003 | Van Schie et al. |
| 2003/0120332 A1 | 6/2003 | Hartley |
| 2003/0130719 A1 | 7/2003 | Martin |
| 2003/0199967 A1 | 10/2003 | Hartley |
| 2003/0233140 A1 | 12/2003 | Hartley et al. |
| 2004/0073289 A1 | 4/2004 | Hartley |
| 2004/0082990 A1 | 4/2004 | Hartley |
| 2004/0098079 A1 | 5/2004 | Hartley et al. |
| 2004/0106978 A1 | 6/2004 | Greenberg et al. |
| 2004/0215327 A1 | 10/2004 | Doig et al. |
| 2004/0225349 A1 | 11/2004 | Thistle et al. |
| 2006/0247761 A1 | 11/2006 | Greenberg |
| 2007/0233222 A1 | 10/2007 | Roeder |
| 2009/0182411 A1 | 7/2009 | Irwin et al. |
| 2010/0100167 A1 | 4/2010 | Bortlein |
| 2013/0116775 A1 | 5/2013 | Roeder et al. |
| 2013/0131777 A1 | 5/2013 | Hartley |
| 2013/0289701 A1 | 10/2013 | Coghlan et al. |
| 2013/0289702 A1 | 10/2013 | Coghlan et al. |
| 2016/0106564 A1 | 4/2016 | Roeder et al. |
| 2017/0112642 A1 | 4/2017 | Hartley et al. |

FOREIGN PATENT DOCUMENTS

| | | |
|---|---|---|
| JP | 2000-279532 A | 10/2000 |
| JP | 2001-129001 A | 5/2001 |
| JP | 2002-500920 A | 1/2002 |
| WO | WO 95/16406 A1 | 6/1995 |
| WO | WO 97/45073 A1 | 12/1997 |
| WO | WO 97/48350 A1 | 12/1997 |
| WO | WO 98/22158 A2 | 5/1998 |
| WO | WO 98/36709 A1 | 8/1998 |
| WO | WO 98/53761 A1 | 12/1998 |
| WO | WO 99/29262 A1 | 6/1999 |
| WO | WO 99/39663 A1 | 8/1999 |
| WO | WO 00/67674 A1 | 11/2000 |
| WO | WO 02/067816 A1 | 9/2002 |
| WO | WO 03/034948 A1 | 5/2003 |
| WO | WO 03/053287 A1 | 7/2003 |
| WO | WO 03/082153 A2 | 10/2003 |
| WO | WO 03/101518 A1 | 12/2003 |
| WO | WO 04/002365 A1 | 1/2004 |
| WO | WO 04/002370 A1 | 1/2004 |
| WO | WO 04/017867 A1 | 3/2004 |
| WO | WO 04/017868 A1 | 3/2004 |
| WO | WO 04/028399 A2 | 4/2004 |
| WO | WO 2005/034808 A1 | 4/2005 |
| WO | WO 2005/122962 A1 | 12/2005 |
| WO | WO 2008/002426 A1 | 1/2008 |
| WO | WO 2008/057568 A1 | 5/2008 |
| WO | WO 2010/111583 A1 | 9/2010 |
| WO | WO 2011/109067 A1 | 9/2011 |
| WO | WO 2013/104324 A1 | 7/2013 |
| WO | WO 2013/104324 A1 | 8/2013 |
| WO | WO 2015/071135 A1 | 5/2015 |
| WO | WO 2015/081175 A1 | 6/2015 |

OTHER PUBLICATIONS

Huynh, T., "Remodeling Of An Acellular Collagen Graft Into A Physiologically Responsive Neovessel", Nature America, Inc., *Nature Biotechnology*, vol. 17, Issue 11, Nov. 1999, pp. 1083-1086.

Office Action received in related U.S. Appl. No. 10/962,765 dated Oct. 23, 2006, 11 pgs.

Amendment and Response Office Action filed in related U.S. Appl. No. 10/962,765 dated Jan. 23, 2007, 10 pgs.

Office Action received in related U.S. Appl. No. 10/962,765 dated Apr. 18, 2007, 10 pgs.

Amendment and Response Office Action filed in related U.S. Appl. No. 10/962,765 dated Aug. 17, 2007, 8 pgs.

Office Action received in related U.S. Appl. No. 10/962,765 dated Nov. 30, 2007, 12 pgs.

Response to Final Office Action filed in related U.S. Appl. No. 10/962,765 dated Jan. 17, 2008, 7 pgs.

Advisory Action received in related U.S. Appl. No. 10/962,765 dated Feb. 4, 2008, 3 pgs.

Amendment and Response Following Advisory Action filed in related U.S. Appl. No. 10/962,765 dated Feb. 28, 2008, 10 pgs.

Notice of Allowance received in related U.S. Appl. No. 10/962,765 dated Jun. 23, 2008, 9 pgs.

Canada Office Action for related Canadian application No. CA 2,540,830, dated Oct. 28, 2010, 3 pgs.

Japanese Grounds of Rejection for related Japanese application No. JP 534458/2006, dated Aug. 3, 2010, 4 pgs.

Japanese Grounds of Rejection for related Japanese application No. JP 534458/2006, dated May 24, 2011, 5 pgs.

International Search Report and Written Opinion for related PCT Application No. PCT/US2004/033568, dated Feb. 2, 2005, 8 pgs.

Written Opinion of the International Preliminary Examining Authority for related PCT Application No. PCT/US2004/033568, dated Aug. 18, 2005, 5 pgs.

(56) References Cited

OTHER PUBLICATIONS

International Preliminary Report on Patentability for related PCT Application No. PCT/US2004/033568, dated Feb. 9, 2006, 4 pgs.
Office Action received for related U.S. Appl. No. 12/228,453 dated Jan. 3, 2011, 9 pgs.
Response to Non-Final Office Action filed in related U.S. Appl. No. 12/228,453 dated Apr. 1, 2011, 6 pgs.
Office Action received for related U.S. Appl. No. 12/228,453 dated May 5, 2011, 7 pgs.
Preliminary Amendment Accompanying Request For Continued Examination filed in related U.S. Appl. No. 12/228,453, dated Oct. 5, 2011, 5 pgs.
Office Action received for related U.S. Appl. No. 12/228,453 dated May 21, 2012, 12 pgs.
Response to Non-Final Office Action filed in related U.S. Appl. No. 12/228,453 dated Oct. 22, 2012, 11 pgs.
Supplemental Response to Non-Final Office Action and Interview Summary filed in related U.S. Appl. No. 12/228,453 dated Nov. 16, 2012, 13 pgs.
Office Action received for related U.S. Appl. No. 12/228,453 dated Jan. 2, 2013, 2 pgs.
Response to Non-Final Office Action filed in related U.S. Appl. No. 12/228,453 dated Feb. 4, 2013, 9 pgs.
Office Action received for related U.S. Appl. No. 12/228,453 dated Mar. 21, 2013, 12 pgs.
Pre-Appeal Conference Request filed in related U.S. Appl. No. 12/228,453 dated Jul. 22, 2013, 5 pgs.
Pre-Appeal Conference Decision received in related U.S. Appl. No. 12/228,453 dated Aug. 13, 2013, 2 pgs.
After Final Pilot Program Response filed in related U.S. Appl. No. 12/228,453, dated Nov. 22, 2013, 8 pgs.
Advisory Action received for related U.S. Appl. No. 12/228,453 dated Dec. 18, 2013, 5 pgs.
Office Action received for related U.S. Appl. No. 12/228,453 dated Feb. 20, 2014, 9 pgs.
Amendment filed in related U.S. Appl. No. 12/228,453, dated May 19, 2014, 10 pgs.
Applicant initiated Interview Summary received in related U.S. Appl. No. 12/228,453, dated Sep. 3, 2014, 4 pgs.
Notice of Allowance in related U.S. Appl. No. 12/228,453, dated Nov. 4, 2014, 10 pgs.
Amendment After Notice of Allowance (Rule 312) in related U.S. Appl. No. 12/228,453, filed Jan. 13, 2015, 8 pgs.
Office Action received in related U.S. Appl. No. 13/759,461 dated Aug. 1, 2013, 12 pgs.
Response to Non-Final Office Action filed in related U.S. Appl. No. 13/759,461 dated Dec. 2, 2013, 10 pgs.
Office Action filed in related U.S. Appl. No. 13/759,461, dated Jan. 16, 2014, 12 pgs.
Pre Appeal Conference Request filed in related U.S. Appl. No. 13/759,461 dated Apr. 16, 2014, 5 pgs.
Pre-Appeal Conference Decision filed in related U.S. Appl. No. 13/759,461 dated May 9, 2014, 2 pgs.
Interview Summary filed in related U.S. Appl. No. 13/759,461, dated Jul. 17, 2014, 3 pgs.
Request for Examination and Amendment filed in related U.S. Appl. No. 13/759,461, dated Aug. 18, 2014, 10 pgs.
Notice of Allowance filed in related U.S. Appl. No. 13/759,461, dated Sep. 18, 2014, 12 pgs.
Office Action in related U.S. Appl. No. 13/950,975, dated Dec. 30, 2013, 10 pgs.
Response to Non-Final Office Action filed in related U.S. Appl. No. 13/950,975, filed Apr. 30, 2014, 12 pgs.
Final Office Action in related U.S. Appl. No. 13/950,975, dated Aug. 28, 2014, 10 pgs.
Amendment filed in related U.S. Appl. No. 13/950,975, filed Jan. 20, 2015, 9 pgs.
Notice of Allowance filed in related U.S. Appl. No. 13/950,975, dated Mar. 24, 2015, 8 pgs.
Partial European Search Report for corresponding EP 15275213, dated Mar. 1, 2016, 4 pgs.
Extended European Search Report for corresponding EP 15275213, dated May 30, 2016, 9 pgs.
European Search Report for corresponding EP 17166079, dated May 11, 2017, 5 pgs.
Examination Report for corresponding European Patent Application No. EP 17166079, dated Oct. 17, 2017, 6 pgs.
Partial European Search Report for corresponding EP 15275213, dated Mar. 1, 2016, 4 pages.
Extended European Search Report for corresponding EP 15275213, dated May 30, 2016, 9 pages.
European Search Report for corresponding European Patent Application No. EP 17166079, dated May 11, 2017, 5 pages.
Examination Report for corresponding European Patent Application No. EP 17166079, dated Oct. 17, 2017, 6 pages.
European Search Report for EP Application No. 18168827.6 dated Jul. 16, 2018, 8 pages.
European Examination Report for EP Application No. 18168827.6 dated Oct. 19, 2018, 6 pages.

\* cited by examiner

SUPPORT STRUCTURE FOR SCALLOPED GRAFTS

RELATED APPLICATIONS

This application claims the benefit of priority of U.S. Provisional Application Ser. No. 62/487,108, filed Apr. 19, 2017, and is a continuation-in-part of U.S. application Ser. No. 14/875,925, filed Oct. 6, 2015, which claims the benefit of priority of U.S. Provisional Application Ser. No. 62/064,595, filed Oct. 16, 2014, all of which are incorporated by reference in their entireties.

TECHNICAL FIELD

The present disclosure relates to a prosthesis such as a stent graft for deployment in a body vessel, including at arterial branching points.

A stent graft is commonly used to reinforce a weakened area in an artery such as an aneurysm. Blood pressure, among other factors, can cause this weakened area to bulge over time. The bulged area can eventually enlarge and rupture if not treated. The stent graft is designed to seal tightly with the artery above and below the aneurysm to allow the blood to flow through the stent graft without causing the weakened area to bulge. When the aneurysm is located in a region of a body lumen adjacent to a branch vessel, the stent graft may need to accommodate the opening to that vessel so that blood flow is not blocked or obstructed. For example, a stent graft may include fenestrations, branches, bare stents and the like to allow blood to flow into a branch vessel.

SUMMARY

The invention is directed to a stent-graft having at least one scallop or cut out in an edge of the graft. The scallop has three sides including a lateral side having a lateral edge. A scallop support structure at least partially conforms to the perimeter of the scallop and has an undulating base that extends below the edge of the scallop and has peaks and valleys. The peaks abut the edge of the scallop and the valleys extend below the edge of the scallop. The scallop support structure has at least two substantially longitudinal perimeter support sections, and the undulating lateral base extends between the at least two substantially longitudinal perimeter support sections. The undulating lateral base has at least two undulations. The two perimeter support sections bound the longitudinal sides. Further aspects of the invention are described here with reference to the drawings.

DRAWINGS

The drawings described herein are for illustration purposes only and are not intended to limit the scope of the present disclosure in any way.

DETAILED DESCRIPTION

In the present application, the term "proximal" refers to a direction that is farthest away from the operator when referring to a delivery device, while the term "distal" refers to a direction that is generally closest to the operator using the delivery device. The distal end of the delivery device is that portion of the device that is intended to remain outside of a patient during a procedure. When referring to the prosthesis itself relative to the delivery device, the proximal end of the prosthesis is that part of the prosthesis nearest the proximal end of the delivery device and the distal end of the prosthesis is that end that is closest to the distal end of the delivery device.

Figure 1:
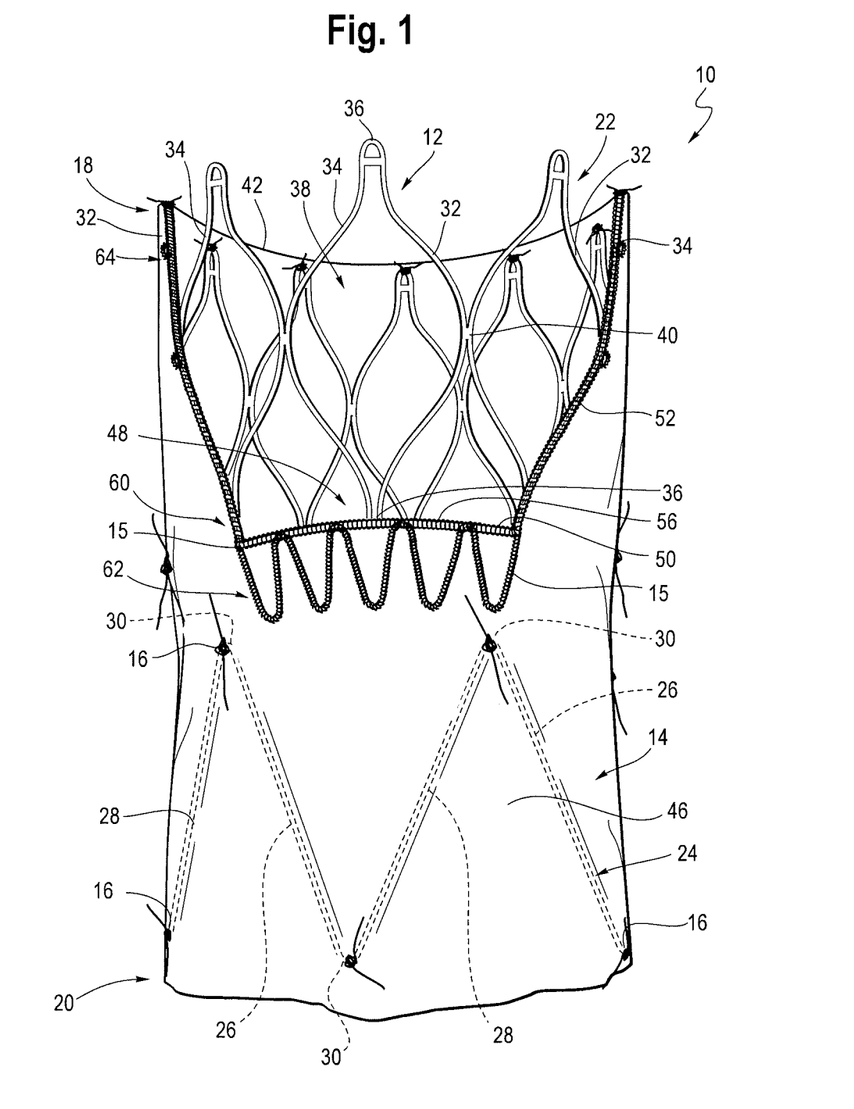
FIG. 1 is a perspective view of a stent graft having a scallop-shaped opening at one end.

FIG. 1 illustrates a portion of a stent graft configured in accordance with a first embodiment of the present disclosure. As shown there, a stent graft 10 includes a stent structure 12, and a tubular graft material 14 attached to the stent structure 12. A suitable stent structure 12 for use in connection with the stent graft 10 described herein may include one or more self-expanding or mechanically-expandable stents or both, and may be deployed according to conventional methodology. A self-expanding stent may be manufactured from stainless steel or a shape-memory alloy, such as nickel titanium alloy (nitinol), cobalt chromium alloy or any other suitable material including cobalt-chromium alloys, amorphous metals, and/or non-metallic materials as would be recognized by one of skill in the art. If the stent comprises a self-expanding material such as nitinol, the stent may be heat-set into the desired expanded state whereby the stent can assume a relaxed radially expanded configuration. Additionally or alternatively, the stent graft 10 may be mechanically expanded, such as through the use of an expandable balloon placed within a lumen of the stent graft 10 and then radially outwardly expanded to thereby expand the stent graft 10.

In one example, the stent structure 12 may include a self-expandable proximal sealing stent 22 to engage a vessel wall when deployed adjacent to a weakened area of the body lumen, or aneurysm. The stent structure 12 may also include one or a series of stents 24 such as z-stents or the like located distal to the proximal sealing stent 22 as shown in FIG. 1. The stent structure 12 may be attached to the interior surface of the graft material 14 or it may be exposed on the exterior of the graft material, or both. The stents may all be the same or they may be different. The stent graft 10 may have any desirable design or configuration depending on the particular use, position of placement in a vessel and/or the procedure being performed. In one example, the stent graft 10 resembles the stent grafts disclosed in U.S. Pat. Nos. 7,413,573, 8,672,993, and 8,702,780, all of which are incorporated by reference in their entirety herein.

Stents at one or both ends of the graft material may be located on the internal surface of at least a portion of the stent graft to provide a smooth outside sealing surface of the graft material against the vessel wall adjacent to the aneurysm as shown in FIG. 1. The tubular graft material 14 may be attached to the stent structure 12 through sutures 16 or any other known attachment mechanisms.

Figure 2:
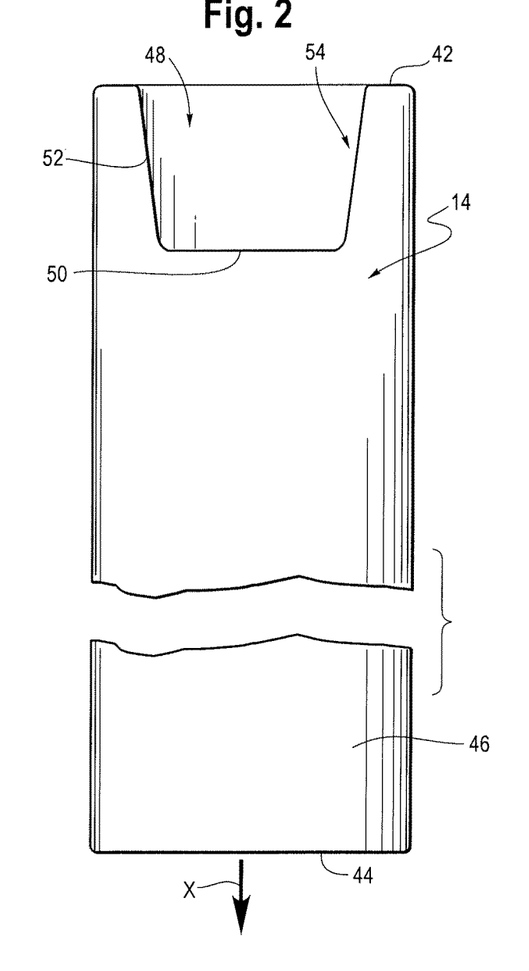
FIG. 2 is a front view of the tubular graft material shown in FIG. 1.

The stent graft 10 includes a proximal end 18 and a distal end 20. As shown in FIG. 2, the tubular graft material 14 defines an elongated tubular body extending between the proximal end 18 and the distal end 20. As will be described in greater detail below, the tubular graft material 14 may have one or more scallop-shaped openings or fenestrations 48 (a "scallop") that are cut out of the material of the stent graft 10. It is also contemplated that the stent graft 10 may be bifurcated at one end to accommodate branch vessels such as the iliac arteries.

FIG. 2 is a front view of the tubular graft material 14 shown in FIG. 1. The tubular graft material 14 may be made of a biocompatible graft material such as polyethylene terephthalate (PET sold under the tradename Dacron®), polyurethane urea optionally blended with a siloxane containing surface modifying additive (such as that sold under the tradename Thoralon®), polytetrafluoroethylene (PTFE) or other synthetic bio-compatible material. A naturally occurring biomaterial, such as collagen, is highly desirable, particularly a specially derived collagen material known as an extracellular matrix (ECM) material, such as small intestinal submucosa (SIS) commercially available from Cook Biotech, West Lafayette, Ind. Besides SIS, examples of ECM's include pericardium, stomach submucosa, liver basement membrane, urinary bladder submucosa, tissue mucosa, and dura mater.

Referring to FIG. 2, the tubular graft material 14 includes a proximal edge 42, a distal edge 44, and a tubular body 46 extending therebetween. The tubular graft material 14 may further define a scallop 48 at one or both ends. In one example, the scallop 48 is formed near the proximal end 18 of the stent graft 10 and the scallop 48 opens to the proximal end 18 of the stent graft 10. In another example (not shown), a scallop 48 is located near the distal edge 44 of the stent graft and opens to the distal end 20 of the stent graft 10 and is otherwise similar to the scallop 48 located near the proximal end 18 of the stent graft 10. In one example, the scallop 48 is positioned to allow blood flow into a branch vessel near the site in which the stent graft 10 is placed in the vasculature.

In one example, scallop 48 may be adjacent to the proximal edge 42. As shown in FIGS. 1-2, the scallop 48 is a cutout portion extending below and distally from the proximal edge 42 of the tubular graft material 14. The scallop 48 is defined by a lateral edge 50 and two opposing longitudinal edges 52. The lateral edge 50 is substantially parallel to the proximal edge 42 of the tubular graft material 14. The opposing longitudinal edges 52 extend generally in a longitudinal direction along the length of the tubular graft material 14 between the proximal edge 42 of the tubular graft material 14 and lateral edge 50 of the scallop 48. The lateral edge 50 and the two opposing longitudinal edges 52 form a perimeter 54 of the scallop 48, which, in one example, defines a generally U-shape configuration. This configuration may expose some of the cells 38 of the proximal stent 22 (as shown in FIG. 1).

Referring back to FIG. 1, the stent structure 12 may include a proximal sealing stent 22 and one or more distal stents 24. The proximal stent 22 and the one or more distal stents 24 may have the same or different structures. In the embodiment illustrated in FIG. 1, the distal stent 24 includes a plurality of first straight struts 26 and a plurality of second straight struts 28 alternately arranged to form a zig-zag ring. The plurality of first and second straight struts 26 and 28 are connected at their opposing ends to form a plurality of connecting ends or apices 30. The tubular graft material 14 may be attached to the distal stent 24 by one or more sutures.

In one example, sutures 16 connect the graft material 14 and the distal stent 24 at the apices 30.

The proximal stent 22 may include a plurality of first curved struts 32 and a plurality of second curved struts 34. The first and second curved struts 32 and 34 are alternately arranged to form a generally elliptical or ring-like configuration. The first and second curved struts 32 and 34 are connected at their opposing ends or apices 36 so that one first curved strut 32 and one adjacent second curved strut 34 form a closed cell 38 having an enlarged middle portion and opposing narrowed portions. The closed cells 38 are connected to at least one point along the sides 40 of the first and second curved struts 32 and 34 to form a ring-like configuration. The apices 36 of the first and second curved struts 32 and 34 may be configured to have generally smooth rounded edges to avoid damaging the vessel lumen wall.

Referring back to FIG. 1, the opposing longitudinal edges 52 of the scallop 48 may be aligned with a portion of the adjacent first and second curved struts 32 and 34 of the proximal stent 22. In the example shown in FIG. 1, the longitudinal edge 52 on the right side of the scallop 48 overlaps a distal portion of the first curved strut 32, whereas the longitudinal edge 52 on the left side of the scallop 48 overlaps a distal portion of the second curved strut 34.

The opposing longitudinal edges 52 of the scallop 48 of the tubular graft material 14 can be stitched by sutures 16 to the first and second curved struts 32 and 34 along at least part of the length of the first and second curved struts 32 and 34. Therefore, the opposing longitudinal edges 52 can conform to a part of the shape of the first and second curved struts 32 and 34.

As described in more detail below, the scallop 48 formed in the tubular graft material 14 may be supported by one or more structures, including a base strut 56 and a support structure 60 that provides additional support for scallop 48. A base strut 56 may be disposed along the lateral edge 50 of the scallop 48. The base strut 56 may be secured to the stent structure 12 and/or the tubular graft material 14 by any known attachment mechanisms. For example, the base strut 56 may be attached to the stent structure 12 and/or the tubular graft material 14 by stitching, gluing, welding, or sutures. In one example, the base strut 56 is sewn along the lateral edge 50 of the scallop 48 to connect the support structure 60 and the tubular graft material 14 at stitch line 15.

The stent graft 10 may further include a support structure 60 to provide additional support for the scallop 48 of the tubular graft material 14. The support structure may be located anywhere on the stent graft 10, and in one example, the support structure is located adjacent to the perimeter of the scallop 48.

The support structure 60 may have any suitable design that preferably corresponds to and/or accommodates the general shape and dimension of the scallop 48. As described below, FIGS. 1 and 3-7 show several embodiments of support structures that can be used to support scallop 48. In one example, the support structure 60 shown in FIG. 1 (and described in greater detail below in connection with FIG. 3) may have a series of zig-zag-shaped segments located distal to the lateral edge 50 of the scallop 48.

The support structure 60 may be secured to the stent structure 12 and/or the tubular graft material 14 by any known attachment mechanisms. For example, the support structure 60 may be attached to the stent structure 12 and/or to the tubular graft material 14 by stitching, gluing, welding, or sutures. In one example, the support structure 60 is sewn onto the graft material 14 along one or more points of the longitudinal edges 52 of scallop 48. The support structure 60 may also be sewn onto the graft material 14 just distal to the lateral edge 50 of the scallop 48.

The support structures described herein may be formed from any biocompatible material such as stainless steel, nickel-titanium alloy (nitinol), ceramic, cobalt/chromium alloys, aluminum or other biocompatible metals and/or composites or alloys such as carbon or carbon fiber. In one example, the support structures are made of stainless steel and are resilient, which allows the stent graft 10 to be delivered to a target site in a compressed configuration and to expand in a deployment configuration.

The support structure 60 (and other support structures disclosed below) may be configured to support the graft material 14. The support structure may also serve to reduce tearing or separation of the graft material 14 from the stent structure 12. In one example, the support structure 60 reinforces the scallop 48 so that blood flow forces do not tear, separate, or disfigure the graft material and/or push the graft material 14 away from or off of the stent structure 12.

In the case of balloon expandable stents, the support structure 60 (and other support structures disclosed below) may provide a more dimensionally stable scallop 48 in the tubular graft material 14, particularly when a balloon expandable stent is used as a leg or side arm extension through a branch vessel (not shown). With the support structure 60, the force of the balloon expansion is less likely to tear the graft material 14 from the stent structure 12.

Figure 3:
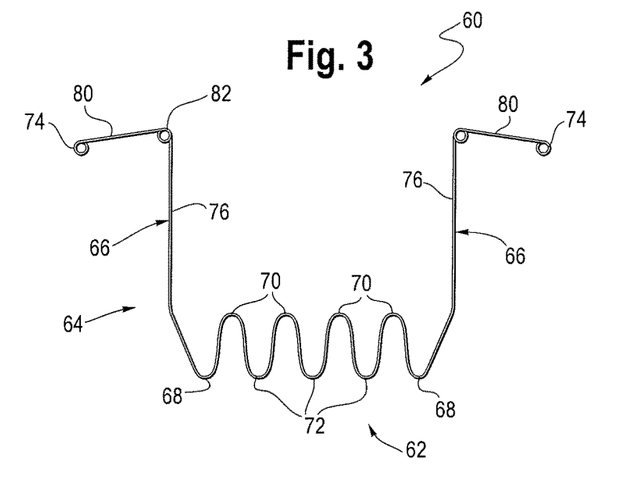
FIG. 3 is a support structure for a scallop-shaped opening shown in FIG. 1.

FIG. 3 illustrates the support structure shown in combination with the stent graft of FIG. 1. Referring to FIG. 3, the support structure 60 includes a lateral base 62 and an attaching member 64. The lateral base 62 includes distal ends 68, a plurality of proximal bends 70 and a plurality of distal bends 72 disposed between the distal ends 68. The lateral base 62 comprises a zig-zag configuration. The attaching member 64 includes a pair of opposing struts 66, which extend from the distal ends 68 of the lateral base 62. The free ends of the opposing struts 66 are formed as a loop 74 to prevent the sharp edges of the opposing struts 66 from damaging the lumen wall.

The support structure 60 may be attached to the stent structure 12 or to the tubular graft material 14, or both. In one example, the lateral base 62 is disposed along the lateral edge 50 of the scallop 48, and as illustrated in FIG. 1, lateral base 62 is disposed distal to the lateral edge 50. No portion of the lateral base 62 protrudes into the opening formed by scallop 48, such that insertion of an extension leg (not shown), if needed, is not blocked and the blood flow through scallop 48 is not obstructed. The plurality of proximal bends 70 are closer to the lateral edge 50 of the scallop 48 than the distal bends 72. The opposing struts 66 of the support structure 60 are disposed generally along the opposing longitudinal edges 52 of the scallop 48.

A portion of the support structure 60 may have a shape that generally conforms to the shape of at least a portion of the first or second curved struts 32 and 34 of stent structure 12. As an example shown in FIG. 3, the opposing struts 66 may have a first segment 76 that generally conforms to the contour of a distal portion of the adjacent first and second curved struts 32 and 34 and a second segment 80 that generally conforms to the contour of the proximal edge 42 of the stent graft material 14. A loop 82 may be formed between the first segment 76 and the second segment 80.

Figure 4:
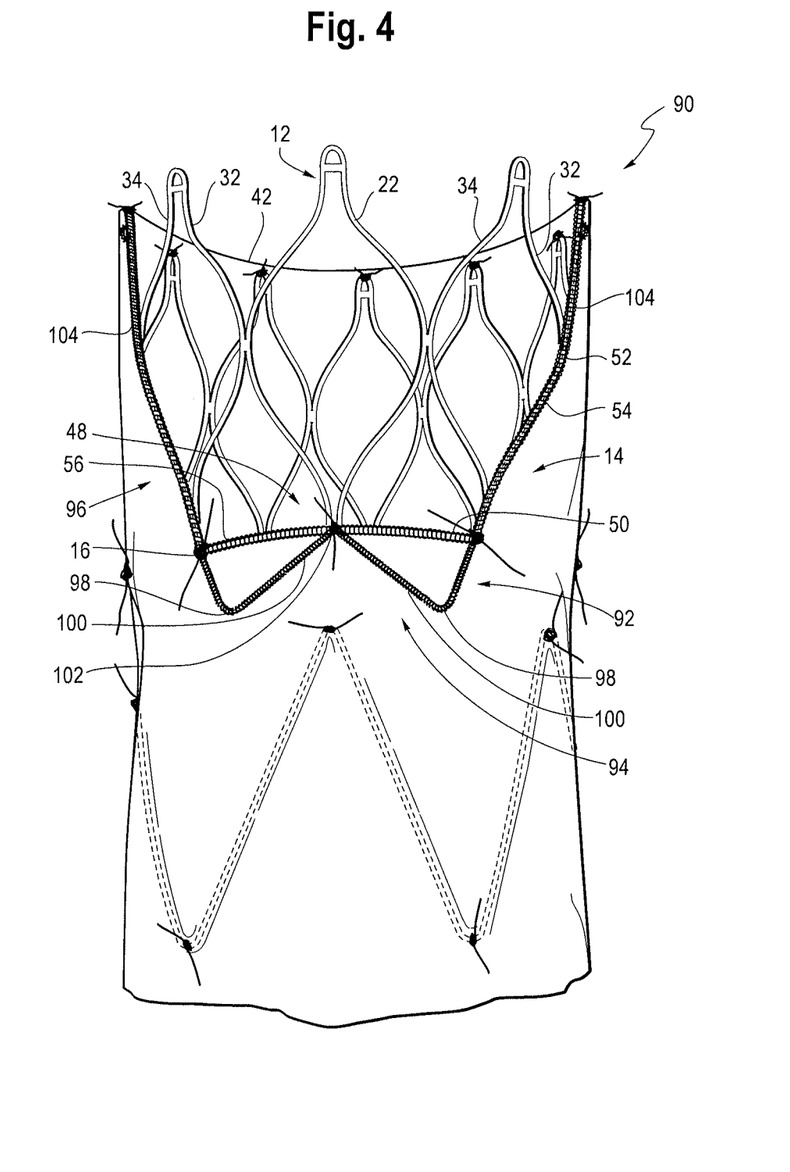
FIG. 4 is a perspective view of a stent graft with another example of a support structure for a scallop-shaped opening in a stent graft.

FIG. 4 is a perspective view of a stent graft 10 constructed in accordance with a second embodiment of the present disclosure. Referring to FIG. 4, a stent graft 90 has a structure similar to that of the stent graft 10 of FIG. 1, except the support structure 60 has a different shape. Therefore, similar reference numerals are used in FIG. 4 for similar components to those in FIG. 1.

The stent graft 90 includes a stent structure 12, a tubular graft material 14, and a support structure 92. Similar to the first embodiment, scallop 48 is formed in the tubular graft material 14 having a perimeter 54 including a lateral edge 50 and opposing longitudinal edges 52. At least a portion of the opposing longitudinal edges 52 extend along a portion of the first and second curved struts 32 and 34.

A base strut 56 is disposed along the lateral edge 50 of the scallop 48. The perimeter 54 of the scallop 48 is attached at one or more points to the first and second curved struts 32, 34 and the base strut 56.

The support structure 92 includes a lateral base 94 and an attaching member 96. The lateral base 94 includes one or more bent segments 98 and an apex 102 between the one or more bent segments 98 that is adjacent to the base strut 56. The attaching member 96 includes a pair of opposing struts 104 extending from the lateral base 94 and disposed generally along the longitudinal edges 52 of the scallop 48. The opposing struts 104 may be attached at one or more points along a portion of the first and second curved struts 32 and 34 of the proximal stent 22. In one example, the opposing struts 104 may also include a first segment 76 and a second segment 80 similar to the opposing struts 66 in FIG. 3.

Similar to support structure 60, the support structure 92 may be secured to the stent structure 12 and/or the tubular graft material 14 by any known attachment mechanism. For example, the support structure 92 may be attached to the stent structure 12 and/or the tubular graft material 14 by stitching, gluing, welding, or sutures. In one example shown in FIG. 4, the support structure 92 is sutured along the perimeter 54 of the scallop 48 and just distal to the scallop 48 to connect the support structure 92 and the tubular graft material 14 at sutures 16.

The support structure 92 may be formed from any biocompatible material such as stainless steel, nickel-titanium alloy (nitinol), ceramic, cobalt/chromium alloys, aluminum or other biocompatible metals and/or composites or alloys such as carbon or carbon fiber. In one example, the support structure 92 is made of stainless steel and is resilient, which allows the scallop 48 and the stent graft 90 to be delivered in a compressed configuration and to expand in a deployment configuration.

Figure 5:
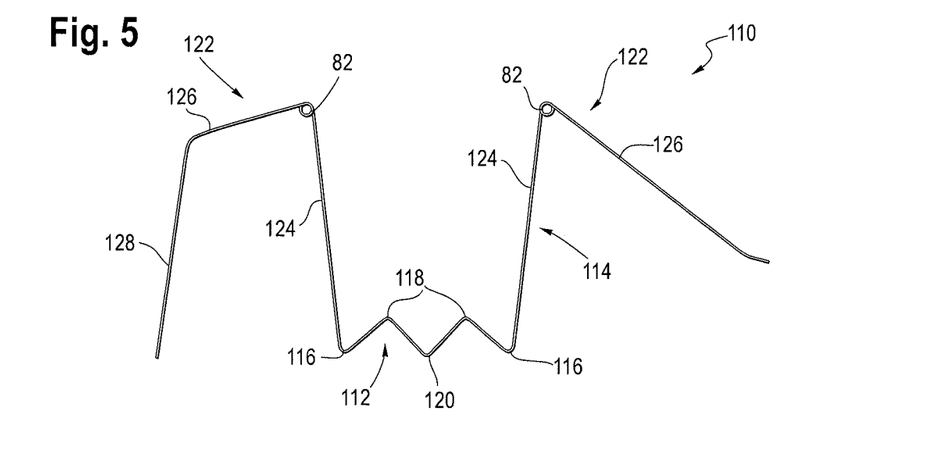
FIG. 5 is another example of a support structure for a scallop-shaped opening in a stent graft.

FIG. 5 is a view of a support structure 110 for a stent graft in accordance with a third embodiment of the present disclosure. Referring to FIG. 5, a support structure 110 can be used with any suitable stent graft, including stent grafts 10 and 90 shown in FIGS. 1 and 4. The support structure 110 includes a lateral base 112 and an attaching member 114. The lateral base 112 defines one or more bent segments 116, a plurality of proximal bends or apices 118, and a distal bend or apex 120 between the one or more bent segments 116. In one example, the lateral base 112 defines a zig-zag configuration. The attaching member 114 includes a pair of opposing struts 122 attached to the one or more bent segments 116.

The opposing struts 122 each include a first segment 124 connected to the one or more bent segments 116 of the lateral base 112, and a second segment 126 connected to an end of the first segment 124. A loop 82 may be formed between the first segment 124 and the second segment 126. One or both of the second segments 126 may further include a third segment 128 connected to the second segment 126. The opposing struts may or may not be symmetrical. For example, as shown in FIG. 5, the opposing struts 122 may not be symmetrical in that only one of the opposing struts 122 has a first segment 124, second segment 126, and a third segment 128. The other of the opposing struts 122 only has a first segment 124 and a second segment 126.

The support structure 110 may be attached to the stent structure 12 and/or the graft material 14. In one example, the first segments 124 may be attached to the graft material 14 along the opposing longitudinal edges 52 of the scallop 48 and/or to at least a portion of the first and second curved struts 32 and 34. The second segment 126 may be disposed along at least a portion proximal edge 42 of the tubular graft material 14. The third segment 128 may be attached along a portion of the first and second curved struts 32 and 34.

The three segments 124, 126 and/or 128 shown in FIG. 5 may be applied to the other support structures in the disclosure. In other words, any of the other disclosed support structures may be modified so that the opposing struts 122 have three segments.

Figure 6:
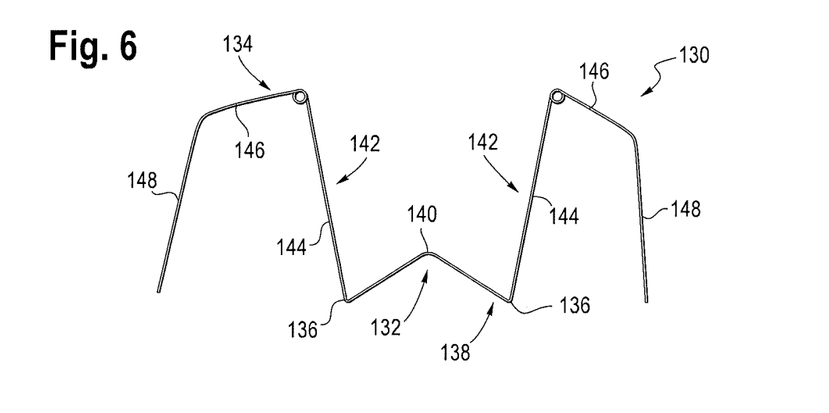
FIG. 6 is a view of another example of a support structure for a scallop-shaped opening in a stent graft.
Figure 7:
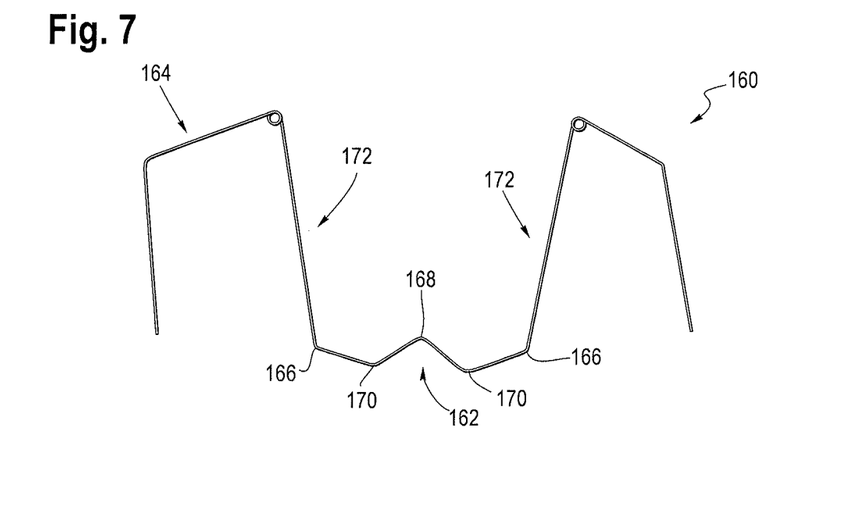
FIG. 7 is a view of another example of a support structure for a scallop-shaped opening in a stent graft.

FIG. 6 is a view of a support structure 130 for a stent graft 10 in accordance with a fourth embodiment of the present disclosure. Referring to FIG. 6, a support structure 130 can be used with any suitable stent graft, including stent grafts 10 and 90 shown in FIGS. 1 and 4. The support structure 130 includes a lateral base 132 and an attaching member 134. The lateral base 132 includes one or more bent segments 136, and one or more distal bends or apices 138 and at least one proximal apex 140. The attaching member 134 includes a pair of opposing struts 142 extending from the one or more bent segments 136 of the lateral base 132. The opposing struts 142 each include a first segment 144, a second segment 146, and a third segment 148. FIG. 7 is a view of a support structure 160 for a stent graft in accordance with a fifth embodiment of the present disclosure. Referring to FIG. 7, a support structure 160 can be used with any suitable stent graft, including stent grafts 10 and 90 shown in FIGS. 1 and 4. The support structure 160 includes a lateral base 162 and an attaching member 164. The lateral base 162 includes one or more bent segments 166, a proximal bend or apex 168 and two distal bends or apices 170. The distal apices 170 may each define an obtuse angle.

Figure 8:
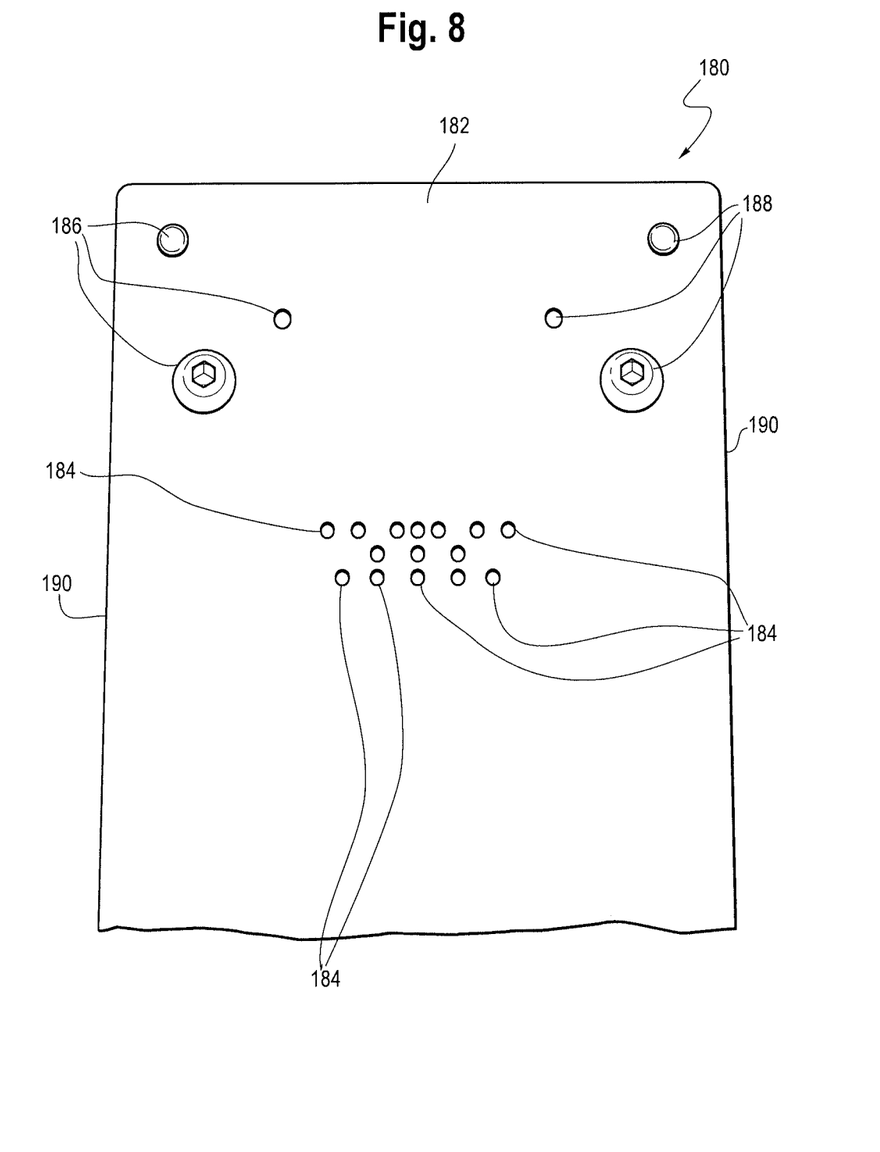
FIG. 8 is an example of a setting fixture for manufacturing a support structure.

The attaching member 164 includes a pair of opposing struts 172 extending from the lateral base 162. FIG. 8 is a schematic view of a setting fixture for manufacturing a support structure in accordance with the teachings of the present disclosure.

The setting fixture 180 shown in FIG. 8 may be used for manufacturing the support structures 60, 92, 110, 130, and 160 used to enforce the scallop 48 of a stent graft. The setting fixture 180 may include a plate body 182 and a plurality of first apertures 184, a plurality of second apertures 186, and a plurality of third apertures 188 through the plate body 182. In one example, the first apertures 184 are located near the center of the plate body 182. The first apertures 184 may be in any arrangement, including in a row or plurality of rows. In one example, the second apertures 186 are located near an edge or corner of the plate 182 and the third apertures 188 are located at an adjacent edge or corner of the plate 182.

The plurality of first apertures 184, second apertures 186 and third apertures 188 may have any number of openings in the plate body 182. In one example, the plurality of first apertures 184 may have 15 openings, the plurality of second apertures 186 may have 3 openings and the plurality of third apertures 188 may have 3 openings in the plate body 182.

The first apertures 184 may be used to set the shape of the lateral base of the support structure, whereas the second apertures 186 and the third apertures 188 may be used to set the two opposing struts of the attaching member of the support structure.

The support structure according to any of the embodiments in this disclosure may be formed by securing one or more wires to the plate body 182 at locations corresponding to one or more of the first, second and third apertures 184, 186, 188 to set the shape of the support structure. In one example, a single wire is used to create the support structure. The shape of the lateral base of the support structure may be set by the first apertures 184 by securing a portion of the wire to the first apertures 184 at predetermined locations. The lateral base may be set to have any shape, including a linear shape, a zig-zag shape, a single curve shape, an arc shape, a triangular shape, or a wavy shape. The lateral base can have any other shape as long as it is disposed distally of the bottom edge of the scallop 48 to provide additional support for the scallop 48. The shape of the opposing struts of the attaching member of the support structure may be set by the second and third apertures 186 and 188 by securing another portion of the wire to the second apertures 186 and the third apertures 188, respectively, at predetermined locations.

After the wire is attached to the setting fixture. 180, the wire may be subject to heat treatment to set the configuration of the support structure. After the support structure is formed, the support structure may be attached to any existing stent graft to provide additional support for a scallop 48.

It should be noted that the disclosure is not limited to the embodiment described and illustrated as examples.

What is claimed is:

1. A stent graft comprising:
   a substantially tubular graft having a first end and a second end;
   a scallop cut out of one or both of the first end and the second end, wherein the scallop extends away from an end edge of the substantially tubular graft and has a perimeter defined by graft material, wherein the perimeter has at least three sides including a lateral side having a lateral edge substantially parallel to the end edge and two longitudinal sides extending between the lateral side and the end edge; and
   a scallop support structure at least partially bounded about the perimeter of the scallop, the scallop support structure comprising at least two substantially longitudinal perimeter support sections, and an undulating lateral base extending between the at least two substantially longitudinal perimeter support sections, wherein the undulating lateral base has at least two undulations;
   wherein one of the at least two perimeter support sections bounds one of the two longitudinal sides and another of the at least two perimeter support sections bounds the other of the longitudinal sides;
   wherein the undulating lateral base is disposed along the lateral side of the scallop and entirely overlaps the graft material, and
   wherein the undulations of the undulating lateral base consist of a plurality of peaks and a plurality of valleys and the plurality of peaks abut the lateral edge of the lateral side and the plurality of valleys extend distally away from the lateral edge of the scallop.

2. The stent graft of claim 1, wherein the undulations of the undulating lateral base consist of at least three peaks abutting the lateral edge and at least two valleys extending away from the lateral edge of the scallop.

3. The stent graft of claim 1, wherein the scallop support structure consists of a single continuous wire.

4. The stent graft of claim 1, wherein the undulations of the undulating lateral base consist of a series of U-shaped undulations.

5. The stent graft of claim 4, wherein end edges of the u-shaped undulations abut the lateral edge of the lateral side.

6. The stent graft of claim 1, further comprising a support wire, separate from the undulating lateral base, wherein the support wire bounds at least the length of the lateral edge of the lateral side and is coincident with the lateral edge of the lateral side.

7. The stent graft of claim 1, wherein the undulations of the undulating lateral base consist of a series of V-shaped undulations.

8. The stent graft of claim 1, wherein the first end of the graft is a proximal end of the graft.

9. The stent graft of claim 1, wherein the second end of the graft is a distal end of the graft.

10. The stent graft of claim 1, wherein the scallop support structure comprises a second lateral base that extends along the lateral side to define the lateral edge.

11. A stent graft comprising:
a substantially tubular graft of graft material having a proximal end, a distal end, a proximal end edge, and a distal end edge;
a scallop cut out of the graft material at the proximal end and having a three sided perimeter including a lateral side having a lateral edge substantially parallel to the proximal end edge and two longitudinal sides extending from the lateral side to the proximal end edge, wherein the scallop extends away from the proximal end edge and toward the distal end; and
a scallop support structure at least partially bounding the perimeter of the scallop, the scallop support structure comprising two substantially longitudinal perimeter support sections, and an undulating lateral base extending between the two substantially longitudinal perimeter support sections, wherein the undulating lateral base comprises a plurality of undulations extending from one of the two substantially longitudinal perimeter support sections to another of the two substantially longitudinal perimeter support sections;
wherein one of the two substantially longitudinal perimeter sections bounds one of the two longitudinal sides of the scallop and another of the two substantially longitudinal perimeter sections bounds the other of the longitudinal sides of the scallop;
wherein the undulating lateral base of the scallop support structure extends distally of the lateral edge of the scallop and entirely overlaps the graft material, wherein the undulating lateral base supports the length of the lateral edge of the scallop, and
wherein the undulations of the undulating lateral base consist of a plurality of peaks and a plurality of valleys and the plurality of peaks abut the lateral edge of the lateral side of the scallop and the plurality of valleys extend distally away from the lateral edge of the scallop.

12. The stent graft of claim 11, wherein the undulations of the undulating lateral base consist of at least three peaks abutting the lateral edge of the scallop and at least two valleys extending away from the lateral edge of the scallop.

13. The stent graft of claim 11, wherein the scallop support structure consists of a single continuous wire.

14. The stent graft of claim 11, wherein the undulations of the undulating lateral base consist of a series of U-shaped undulations.

15. The stent graft of claim 14, wherein end edges of the u-shaped undulations abut the lateral edge of the lateral side of the scallop.

16. The stent graft of claim 11 further comprising a support wire, separate from the undulating lateral base, wherein the support wire bounds the length of the lateral edge of the lateral side of the scallop.

17. The stent graft of claim 11, wherein the undulations of the undulating lateral base consist of a series of V-shaped undulations.

18. A stent graft comprising:
a substantially tubular graft having a first end and a second end and a plurality of stents along a length of the tubular graft from the first end to the second end;
a scallop cut out of one or both of the first end and the second end, wherein the scallop extends away from an end edge of the substantially tubular graft and has a perimeter defined by graft material, wherein the perimeter has at least three sides including a lateral side having a lateral edge substantially parallel to the end edge and two longitudinal sides extending between the lateral side and the end edge; and
a scallop support structure at least partially bounded about the perimeter of the scallop, the scallop support structure comprising at least two substantially longitudinal perimeter support sections, and an undulating lateral base extending between the at least two substantially longitudinal perimeter support sections, wherein the undulating lateral base has at least two undulations;
wherein one of the at least two perimeter support sections bounds one of the two longitudinal sides and another of the at least two perimeter support sections bounds the other of the longitudinal sides;
wherein the undulating lateral base is disposed along the lateral side of the scallop and entirely overlaps the graft material, and
wherein the scallop support structure is a separate structural element from any of the plurality of stents.

19. The stent graft of claim 18, wherein the scallop support structure does not extend about the circumference of the stent graft.

* * * * *

UNITED STATES PATENT AND TRADEMARK OFFICE
CERTIFICATE OF CORRECTION

| | |
|---|---|
| PATENT NO. | : 10,959,826 B2 |
| APPLICATION NO. | : 15/956034 |
| DATED | : March 30, 2021 |
| INVENTOR(S) | : Skender et al. |

Page 1 of 1

It is certified that error appears in the above-identified patent and that said Letters Patent is hereby corrected as shown below:

On the Title Page

In (73) Assignee, delete "Cook Medical Technology LLC" and replace with --Cook Medical Technologies LLC--.

Signed and Sealed this
Thirteenth Day of September, 2022

Katherine Kelly Vidal
*Director of the United States Patent and Trademark Office*